US009668990B1

(12) United States Patent
Yang et al.

(10) Patent No.: US 9,668,990 B1
(45) Date of Patent: Jun. 6, 2017

(54) BENZENESULFONAMIDES COMPOSITIONS FOR TREATMENT OF MALIGNANT PLEURAL EFFUSIONS

(71) Applicant: GONGWIN BIOPHARM HOLDINGS CO., LTD., Taipei (TW)

(72) Inventors: Chuan-Ching Yang, Taipei (TW); Mao-Yuan Lin, Taipei (TW)

(73) Assignee: Gongwin Biopharm Holdings Co., Ltd., Grand Cayman (KY)

( * ) Notice: Subject to any disclaimer, the term of this patent is extended or adjusted under 35 U.S.C. 154(b) by 0 days.

(21) Appl. No.: 15/179,153

(22) Filed: Jun. 10, 2016

(51) Int. Cl.
*A61K 31/18* (2006.01)
*A61K 45/06* (2006.01)

(52) U.S. Cl.
CPC ............ *A61K 31/18* (2013.01); *A61K 45/06* (2013.01)

(58) Field of Classification Search
None
See application file for complete search history.

(56) References Cited

U.S. PATENT DOCUMENTS

| 6,471,974 B1 * | 10/2002 | Rees | A01N 59/00 |
| | | | 252/187.25 |
| 2003/0022843 A1 * | 1/2003 | Wu | A61K 31/18 |
| | | | 514/23 |

FOREIGN PATENT DOCUMENTS

| CN | 101485644 | * | 7/2009 |
| CN | 101940708 | A | 1/2011 |
| CN | 104056104 | A | 9/2014 |
| CN | 105267751 | A | 1/2016 |
| CN | 105311599 | A | 2/2016 |
| CN | 104922528 | A | 6/2016 |

OTHER PUBLICATIONS

Dosage Forms: Non Parenteral in Encyclopedia of Pharmaceutical Technology, Singh et al., Marcel Dekker, Inc. 2008.*
Machine Translation of CN 101485644, 2008.*
Gao et al., J. Thorac Dis, 2013, 5(4), pp. 472-483.*
Gao, "Antitumor Effect of Para-Toluenesulfonamide Against Lung Cancer Xeongraft in a Mouse Model", State Key Laboratory of Respiratory Disease; Beijing Vision Drugs Development Limited, Beijing China, Aug. 28, 2013, pp. 472-483.

* cited by examiner

*Primary Examiner* — Karl J Puttlitz

(74) *Attorney, Agent, or Firm* — Kramer Amado P.C.

(57) ABSTRACT

The present disclosure provides a novel pharmaceutical composition for treating a malignant pleural effusion (MPE), including a benzenesulfonamide derivative and a pharmaceutically acceptable excipient. The present disclosure further provides a method for treating MPE by using the pharmaceutical composition.

9 Claims, No Drawings

BENZENESULFONAMIDES COMPOSITIONS FOR TREATMENT OF MALIGNANT PLEURAL EFFUSIONS

BACKGROUND OF THE INVENTION

1. Field of the Invention

The present disclosure relates to a method for treating malignant pleural effusions (MPE) in a subject, particularly for treating MPE in a subject suffering from lung cancer, breast cancer, lymphoma, leukemia, or mesothelioma in a late stage by a novel pharmaceutical composition comprising benzenesulfonamides. The present disclosure also relates to a pharmaceutical composition comprising benzenesulfonamides and a process for preparation thereof.

2. Description of Related Art

Cancers with various origins have been serious diseases worldwide. The later stage of cancer is diagnosed, the lower cure rate is. Malignant pleural effusions (MPE) resulted from metastatic malignant pleural tumors or primary malignant pleural tumors is one of the most common complication of malignant tumors. It is reported that 24% to 50% of exudative pleural effusions originated from malignant lesions and 50% of tumor metastasis finally lead to MPE. Top three MPE generating cancers are lung cancer the first, breast cancer the second, and lymphoma the third. The primary cancer tumor lesions have not been found in about 5% to 10% of MPE cases. All malignant tumors excluding primary brain tumor and limbs tumor may generate MPE (*Am J Respir Crit Care Med* Vol. 162. P. 1987-2001, 2000).

MPE is often regarded as a complication in the late stage of tumors. MPE is rapidly developing and often complicated with the symptoms such as chest tightness, shortness of breath, palpitations, and unable supine. Delaying the treatment of MPE might cause barriers of respiration and circulation, hypoproteinemia, and anemia, and the severe symptoms might be life-threatening. Therefore, rapidly and effectively treating MPE is an important step in cancer therapy. However, the treatment of MPE is difficult due to high mortality rate. The one, three and six-month(s) mortality rates of patients with MPE are 50%, 60%, and 82%, respectively. The average life expectancy is merely 3.1 months. Effectively managing MPE has been one of the difficult issues in clinical treatments.

In clinical practice, removing pleural effusions and preventing its accumulation again, relieving symptoms, raising life quality, as well as extending survival period are the current main treatments for MPE. The major methods include chest drainage, video-assisted thoracic surgery (VATS), intrathoracic administration, pleural fixation, whole body chemotherapy, radiotherapy, thermal therapy and the like. However, limitation exists in each treatment application which results in limited therapy efficacy. Recently hyperthermic pleural perfusion treatment provides a new method and it is theoretically and technically supported. There are two kinds of hyperthermic pleural perfusion treatments: one is physiological saline, which exhibits low timeliness to pleural effusions control and high recurrence; the other is chemotherapy by cisplatin and so on, which is used for local anti-cancer and promoting pleural connection. However, over pleural connections are frequently observed in clinical practice, resulting in fibrin depositing on pleura, pleural capillaries and fibroblasts extending into fibrin and forming granulation tissue, gradually thickening to dense envelope and forming pleural fibreboard. The wide and rigid fibreboard wraps around the lung tissue and lacks flexibility, so as to limit chest expansion, severely reduce breath and increase the recurrence rate of pleural effusions. As a result, a pleural perfusion liquid effectively improving function of respiratory system and reducing recurrence rate remains a need yet to be met.

MPE is a secondary symptom of primary tumor. Therefore, the attention of clinical study and the improvement of treatment are relatively limited compared to other mainstream domains of tumor study. Meanwhile, the commercial profit is also limited. In view of the above problem of the conventional art, the technical purpose of the present disclosure is to provide a new medication with assured effect and fewer side effects to treat MPE. The study on MPE by benzenesulfonamides is so far underreported.

Chinese Patent Application No. 201010284152.0 discloses a Chinese medicine for treating MPE comprising the following Chinese herbs: *Codonopsis pilosula* 13-18 g, *Astragalus membranaceus* 28-32 g, prepared rhizome of *Rehmannia glutinosa* 13-18 g, *Angelica sinensis* 13-18 g, *Fritillaria cirrhosa* 8-12 g, *Wolfiporia extensa* 13-18 g, *Semen lepidii* 8-12 g, licorice 8-12 g, Chenpi 8-12 g, *Trichosanthes kirilowii* Maxim. 13-18 g, grifola 8-12 g, *Rhizoma alismatis* 8-12 g, the root of *Paris polyphylla* 8-12 g, *Solanum lyratum* 8-12 g.

Chinese Patent Application No. 201410315790.2 discloses a medical composition for treating MPE comprising the following Chinese herbs: *Jacobinia suberecta* 20-30 parts, herb of *Villosulous veronicastrum* 9-15 parts, *Potentillae parvifoliae* fisch 5-15 parts, *Iris japonica* 25-30 parts, *Wusili dragonflyorchis* rhizome 10-16 parts, *Phaenosperma globosa* 15-25 parts, *Chorion ovi* 3-8 parts, root of *Dunn Antictrema* 7-10 parts, *Manyflower solomonseal* rhizome 10-15 parts, *Paris polyphylla* 15-25 parts, *Solanum lyratum* 20-25 parts, *Duchesnea indica* 15-20 parts.

Chinese Patent Application No. 201510413494.0 discloses a medical composition for treating MPE comprising the following Chinese herbs: *Panax quinquefolius* 2-18 parts, *Panax pseudo-ginseng* 4-30 parts, *Semen lepidii* 2-18 parts, *Pyrrosla lingua* 3-21 parts, *Zanthoxylum bungeanum* Maxia. 2-8 parts, *Cynanchi paniculati* 10-50 parts, *Trichosanthes kirilowii* Maxim., 5-25 parts, fresh *Astragalus* 10-50 parts, *Rhizoma alismatis* 2-18 parts, *Atracylodes macrocephalae* 3-21 parts, *Ziziphus jujuba* Mill. 2-12 parts.

Chinese Patent Application No. 201510776648.2 discloses a medication for treating chi yin deficiency type MPE, comprising *Codonopsis pilosula*, *Eleutherococcus senticosus*, *Scrophularia ningpoensis* Hemsl., *Plantago asiatica* L., *Semen lepidii*, Ephedra, *Ramulus Cinnamomi*, *Rheum Palmatum* L., *Morus alba*, root of *Dioscorea polystachya*, *Orchis italica*, *Curculigo orchioides*, *Levisticum officinale*, root of *Asparagus cochinchinensis*, Japanese Honeysuckle, *Ruta graveolens*, *Aster ageratoides* Turcz., and *Typha angustifolia* L.

Chinese Patent Application No. 201510772076.0 discloses a medication for treating spleen phlegm type MPE, comprising *Rheum palmatum* L., *Semen lepidii*, roots of *Curcuma wenyujin*, *Ramulus Cinnamomi*, fruit of Large flower *Gardenia*, *Iphigenia indica* Kunth, *Prunella vulgaris*, *Codonopsis pilosula*, *Zingiber oj-jicinale* Rosc., *Schisandra chinesis*, cattle penis, oriental dodartia herb, *Platycodon grandiflorus*, *Levisticum officinale*, Ephedra, *Liriope spicata*, fruits of *Arctium lappa* L., Largehead atractylodes rhozome, *Scrophularia ningpoensis* Hemsl., *Acorus tatarinowii* Schott., and licorice.

There are certain methods in treating MPE by Chinese medicine based on five compound medications described above, but their clinical evidences of treating MPE are not sufficient yet. As such, the efficient results of the clinical treatment are hardly achieved due to the defect of five patented medications described above.

SUMMARY OF THE INVENTION

In one aspect of the present disclosure, a pharmaceutical composition for treating malignant pleural effusions (MPE) is provided. The pharmaceutical composition comprises a benzenesulfonamide derivative and a pharmaceutically acceptable excipient.

In one embodiment of the present disclosure, the benzenesulfonamide derivative may be a compound represented by formula (I):

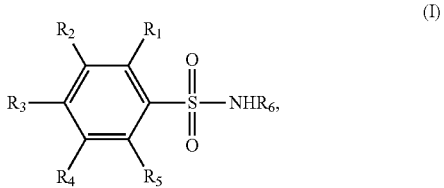

wherein $R_1$-$R_6$ are each independently selected from the group consisting of H, C1-C6 linear or branched alkyl, C1-C6 linear or branched alkoxy, amino, halo, halo-substituted C1-C6 linear or branched alkyl, and sulfonamide group.

In one embodiment of the present disclosure, the compound of formula (I) may be selected from the group consisting of p-toluenesulfonamide or o-toluenesulfonamide, N-ethyl-p-toluene sulfonamide, N-ethyl-o-toluene sulfonamide, N-cyclohexyl-p-toluene sulfonamide and a combination thereof.

In one embodiment of the present disclosure, the benzenesulfonamide derivative may be present in an amount ranging about 10%-50% by weight. In one embodiment of the present application, the pharmaceutical composition may comprise 10%-50% by weight of the benzenesulfonamide derivative, 10%-40% by weight of PEG-400, 5%-10% by weight of 1,2-propylene glycol, 1%-5% by weight of sebacic acid, 10%-20% by weight of 2-ethyl-1,3-hexanediol, 0%-10% by weight of dimethyl sulfoxide and 0%-10% by weight of ethanol.

In another aspect of the present disclosure, the method for treating malignant pleural effusions is provided. The method comprises administering a therapeutically effective amount of the pharmaceutical composition comprising a benzenesulfonamide derivative to a subject in need thereof.

In one embodiment of the present disclosure, the pharmaceutical composition may be administered to the subject intratumorally, intravenously, subcutaneously, intradermally, orally, intrathecally, intraperitoneally, intranasally, intramuscularly, intrapleuraly, or through nebulization. In another embodiment of the present disclosure, the pharmaceutical composition is administered intrapleuraly to the subject.

In one embodiment of the present disclosure, the subject may be suffering from cancer, such as lung cancer, breast cancer, lymphoma, leukemia, and mesothelioma.

In one embodiment of the present disclosure, the method further comprises administering at least one additional MPE therapy to the subject. The additional MPE therapy may be selected from chest drainage, video-assisted thoracic surgery (VATS), intrathoracic administration, pleural fixation, whole body chemotherapy, radiotherapy, or thermal therapy.

DETAILED DESCRIPTION OF THE PREFERRED EMBODIMENTS OF THE INVENTION

The following examples are used to exemplify the present disclosure. A person of ordinary skills in the art can understand the other advantages of the present disclosure, based on the disclosure of the specification of the present disclosure. The present disclosure can also be implemented or applied as described in different specific examples. It is possible to modify and or alter the examples for carrying out this disclosure without contravening its spirit and scope, for different aspects and applications.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a pharmaceutical composition comprising a therapeutically effective amount of benzenesulfonamides as a medicament for MPE and also provides a process for preparing the above composition and a treatment method using the composition.

The pharmaceutical composition of benzenesulfonamides for treating MPE comprises, for example, p-toluenesulfonamide or o-toluenesulfonamide, N-ethyl-p-toluene sulfonamide, N-ethyl-o-toluene sulfonamide, N-cyclohexyl-p-toluene sulfonamide, or other toluenesulfonamides or a combination of two or more in any ratio of different toluenesulfonamides. The monomer of each benzenesulfonamide is in white crystal form.

The benzenesulfonamides may be represented by the following formula (I):

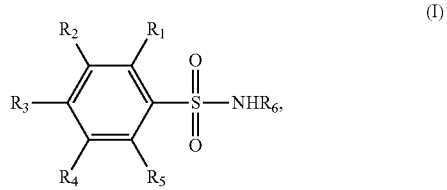

wherein $R_1$-$R_6$ are each independently selected from the group consisting of H, C1-C6 linear or branched alkyl, C1-C6 linear or branched alkoxy, amino, halo, halo-substituted C1-C6 linear or branched alkyl, and sulfonamide group. Preferably, $R_1$-$R_6$ are each independently H, methyl or ethyl.

The pharmaceutically acceptable excipient included in the pharmaceutical composition of the present disclosure may be conventional pharmaceutical carriers, such as filler, binder, preservative, disintegrating agent, lubricant, suspending agent, wetting agent, solvent, surfactant, acids and flavoring agent.

The binders that are suitable for use in the present disclosure may be starch paste, sorbitol, guar gum, polyvinyl pyrrolidone, cellulose derivatives such as hydroxy propylmethyl cellulose, sodium carboxymethyl cellulose, carbomer (commercially available as carbopols) etc.

The preservatives suitable for use in the present disclosure may be sodium benzoate, methyl paraben, propyl paraben, cresols, etc.

The lubricants that are suitable for use in the present disclosure may be metallic stearates such as magnesium, calcium and sodium stearates, stearic acid, talc, polyethylene glycols, soluble salts such as sodium chloride, sodium benzoate etc.

The wetting agents that are suitable for use in the present disclosure may be glycerol, sorbitol, polypropylene glycol etc.

The flavoring agents that are suitable for use in the present disclosure may be peppermint oil, menthol, lemon oil, orange oil, and cinnamon oil.

Preferably, the pharmaceutically acceptable excipient may be polyethylene glycol (PEG), alkylene glycol, sebacic acid, and/or dimethyl sulfoxide, alcohols. More preferably, the pharmaceutical compositions may comprise the following parts by weight:

| Pharmaceutical composition of benzenesulfonamides (GNW-601) | |
|---|---|
| Sulfa drugs | 10%-50% |
| PEG-400 | 10%-40% |
| 1,2-propylene glycol | 5%-10% |
| Sebacic acid | 1%-5% |
| p-toluenesulfonic acid | 1%-15% |
| 2-ethyl-1,3-hexanediol | 10%-20% |
| Dimethyl sulfoxide | 0-10% |
| Ethanol | 0-10% |

The present disclosure also provides the process for the preparation of pharmaceutical composition.

The process includes: adding and mixing the solvents and adjuvants in a given ratio; heating the mixture to 80° C. to 110° C. with stirring to form a clear oily liquid; gradually adding the sulfa drug with stirring until completely dissolved; filtering and cooling the mixture to obtain the composition of the present disclosure in an oily liquid form (GNW-601).

The process for preparing the injection formulation of GNW-601 may be carried out based on the technique known in the art, for example, by adding adjuvants or and solvents, and further adjusting the mixture to isotonic condition. For example, microporous filters can be used for the step of filtering in the process.

The pharmaceutical composition of benzenesulfonamides may be formulated into a form suitable for parenteral administration, injection, continuous infusion, sublingual administration, subcutaneous administration or oral administration. In one embodiment of the present disclosure, the pharmaceutical composition may be in a form selected from the group consisting of a formulated to injection, dry powders, tablets, oral liquid, wafers, films, lozenges, capsules, granule, and pill.

For example, GNW-601 for treating MPE can be a solution form and administered to a subject by intramuscular or intrapleural injection or by oral or other routes. GNW-601 also can be other formulation for the oral administration as a medicament for treating MPE. The intrapleural injection dosage for MPE treatment is 3-8 mL/injection (about 990-2640 mg), twice per week with 4-week period as a course.

The injection dosage for adults is 1000 mg-1800 mg of p-toluenesulfonamide or other benzenesulfonamides. The oral dosage is 150-1800 mg of p-toluenesulfonamide or other benzenesulfonamides per day.

The present disclosure provides the use of GNW-601 as a medicament for treating MPE.

By the long-term clinical trials, it is proven that the pharmaceutical composition of the present disclosure can improve the clinical symptoms and the life quality of MPE patients. The pharmaceutical composition of the present disclosure is preferably a targeted prescription with the efficacy to the best performance compared to current available medications for treating MPE.

EXAMPLE

Efficacy of MPE Treatment by the Present Disclosure in Clinical Trials

The clinical trial was conducted at the First Affiliated Hospital of Guangzhou Medical College from September 2006 to March 2009 and October 2011 to December 2013. Total 46 cases with MPE were enrolled, there were 16 male and 30 female, aged from 19 to 83 years, and their average age was 54.80±11.62 years. There were 22 cases of squamous cell carcinoma, 18 cases of lung adenocarcinoma, 3 cases of pleural metastasis in breast cancer, and 3 cases of pleural metastasis from primary liver cancer based on histology examination.

Diagnostic criteria: A. patients with advanced cancer, breathing difficulties, chest tightness, and flatness by auscultation, B. chest radiography, B ultrasound, CT scan confirmed MPE, C. pleural effusion, histopathological or cytological examination revealed malignant cells, D. pleural effusion with CEA value >10-12 ng/mL, E. exclusion of other causes of pleural effusion.

Inclusion criteria: A. at least one imaging (CT, X ray, or B ultrasound) showing the quantity of MPE within 2 weeks from enrollment, B. confirmed MPE by histological or cytological diagnosis, C. normal functions of liver, kidney, and blood, D. Karnofsky score ≥50, expected survival time ≥3 months, E. no interstitial pneumonia or pulmonary fibrosis, F. excluding diagnostic puncture, no treatment of chemotherapy and intrapleural medication injection within one month before enrollment, G. informed consent forms signed by patients or their family members.

Exclusion criteria: A. end-stage patients with cachexia and severe hypoalbuminemia; Karnofsky score ≥50, unable to complete one course of treatment, B. basal treatment combined with other anti-cancer therapies, C. other causes of pleural effusions such as infections and cardiopathy, D. pregnant women, or mental disorders, or those not following the treatment scheme.

Meeting at least one of the following criteria should be withdrawn from the clinical trial: A. rapidly deterioration or death during trial, B. patient condition or patient himself requesting stop of treatment before completion of a course, C. those poorly complying with scale fill, D. not meeting inclusion criteria after enrollment.

Treatment methods: before GNW-601 administration, remove MPE was performed with the intrathoracic injection needle one or two times (800-1400 mL per day) when necessary. GNW-601 was intrathoracically injected 3-8 mL (about 990-2,640 mg), two times per week with 4-week as one course. On average, patients were conducted for four times of treatment.

Response Evaluation Criteria:

Evaluation criteria of remission of pleural effusion were based on term effect in accordance with the provisions of WHO standards. Complete remission (CR): pleural effusion completely disappeared and maintained for at least 4 weeks; partial remission (PR): pleural effusion significantly reduced (≥50% reduction) and maintained for 4 weeks; stable (SD):

pleural effusion decreased without increasing trend; progress (PD): no reduction or increase in pleural effusion. The total efficacy: CR+PR.

Evaluation criteria of life quality were according to WHO universal Karnofsky performance status scale. The improvement was defined as 10 or more points increase after treatment and the reduction was defined as 10 or more points decrease after treatment. Those increase or decrease less than 10 points were defined as stable. Clinical benefit rate: improvement+stable.

Clinical evaluation and scoring criteria included guiding patients to fill in case report forms based on the severity of symptoms (dyspnea, cough, chest pain, weight loss, coughing up blood and sputum, lassitude, loss of appetite, etc.), grading from 0 to 6 points as a counterpart symptom score (the higher the score, the more severe the symptoms), and recording and comparing the score difference before and after treatment for each patient in the group to confirm the efficacy of treatments (the greater the score difference, the greater the improvement).

Adverse reactions were reported according to the grading standards of common adverse reactions in clinical trials issued by WHO in 1989, focusing on observation of nausea, vomiting, diarrhea and other gastrointestinal reactions, as well as leukopenia and bone marrow suppression.

Observation Methods:

Outcome measures included: A. general recording items, B. relieved conditions of pleural effusion, C. the changes in the life quality, D. the changes in clinical grading scores, E. adverse reactions including gastrointestinal reactions, bone marrow suppression, effects on the functions of liver and kidney.

Observation time points: recording the general items upon enrollment (e.g., name, gender, age, duration of disease, primary tumor pathology, and pleural effusion and its position, syndromes and Karnofsky score), weekly measuring blood and blood biochemistry for four weeks, filling case reports one day before treatment and seven days after the treatment, and determining the actual MPE relieved condition one month after treatment. The reduction of MPE was verified by X ray or B ultrasound.

Treatment results: after two courses of treatment, the following results were revealed in 46 patients:

Term effects: complete remission (CR) 24 cases, partial remission (PR) 9 cases, stable (SD) 7 cases, progress (PD) 6 cases; the total efficacy is 71.7/0 (33/46).

Life quality: life quality was improved in 40 cases, stable in one case, reduction in five cases; the clinical benefit rate was 87.0% (40/46).

Adverse reactions: there was no observed adverse reaction over grade III; main side effects included drowsiness, fatigue and loss of appetite. Ten patients had fever (37.5° C. to 38° C.). All symptoms disappeared within 12 hours. None of the usual side effects, such as pain, nausea and hair loss, was found. There were no observed abnormalities in hematology and renal functions during and after treatment.

CONCLUSIONS

The pharmaceutical composition of the present disclosure can treat MPE, and improves the life quality and clinical symptoms of MPE patients. No significant increase in adverse reactions was found.

What is claimed is:

1. A method for treating a malignant pleural effusion (MPE), comprising
administering a pharmaceutical composition to a subject in need thereof, wherein the pharmaceutical composition comprises a benzenesulfonamide derivative represented by a compound of formula (I):

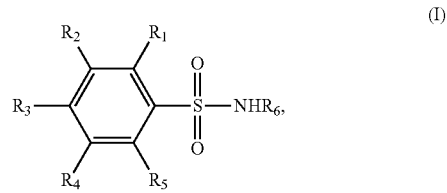

wherein $R_1$ to $R_6$ are each independently selected from the group consisting of H, C1-C6 linear or branched alkyl, C4-C6 linear or branched alkoxy, amino, halo, halo-substituted C1-C6 linear or branched alkyl, and sulfonamide group; and
administering at least one additional MPE therapy, wherein the at least one additional MPE therapy is chest drainage.

2. The method according to claim 1, wherein the benzenesulfonamide derivative in the pharmaceutical composition is administered to the subject in a therapeutically effective amount of from about 1000 mg to about 1800 mg per day.

3. The method according to claim 1, wherein the pharmaceutical composition is administered to the subject intratumorally, intravenously, subcutaneously, intradermally, orally, intrathecally, intraperitoneally, intranasally, intramuscularly, intrapleurally, or through nebulization.

4. The method according to claim 1, wherein the subject is suffering from cancer.

5. The method according to claim 4, wherein the cancer is at least one selected from the group consisting of lung cancer, breast cancer, lymphoma, leukemia, and mesothelioma.

6. The method according to claim 1, wherein the additional MPE therapy is further consists of video-assisted thoracic surgery (VATS), intrathoracic administration, pleural fixation, whole body chemotherapy, radiotherapy, or thermal therapy.

7. The method according to claim 1, wherein the compound of formula (I) is selected from the group consisting of p-toluenesulfonamide, o-toluenesulfonamide, N-ethyl-p-toluene sulfonamide, N-ethyl-o-toluene sulfonamide, N-cyclohexyl-p-toluene sulfonamide and a combination thereof.

8. The method according to claim 1, wherein the benzenesulfonamide derivative is present in the pharmaceutical composition in an amount ranging from about 10% to about 50% by weight.

9. The method according to claim 8, wherein the pharmaceutical composition further comprises at least one of 10%-40% by weight of PEG-400, 5%40% by weight of 1,2-propylene glycol, 1%-5% by weight of sebacic acid, 10%-20% by weight of 2-ethyl-1,3-hexanediol, 0%-10% by weight of dimethyl sulfoxide and 0%-10% by weight of ethanol.

* * * * *